(12) United States Patent
Bedoukian

(10) Patent No.: US 8,349,310 B2
(45) Date of Patent: Jan. 8, 2013

(54) ATTRACTANT COMPOSITIONS AND METHOD FOR ATTRACTING BITING INSECTS

(75) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 393 days.

(21) Appl. No.: 12/451,734

(22) PCT Filed: May 27, 2008

(86) PCT No.: PCT/US2008/006696
§ 371 (c)(1),
(2), (4) Date: Nov. 27, 2009

(87) PCT Pub. No.: WO2008/150396
PCT Pub. Date: Dec. 11, 2008

(65) Prior Publication Data
US 2010/0115825 A1    May 13, 2010

Related U.S. Application Data

(60) Provisional application No. 60/932,064, filed on May 29, 2007.

(51) Int. Cl.
*A01N 25/00* (2006.01)
*A01N 59/04* (2006.01)
*A01N 65/00* (2009.01)
*A61K 33/00* (2006.01)
*A61K 36/54* (2006.01)

(52) U.S. Cl. ............ 424/84; 424/405; 424/699; 424/739
(58) Field of Classification Search .................... 424/84, 424/405
See application file for complete search history.

(56) References Cited

U.S. PATENT DOCUMENTS

| 4,189,614 A * | 2/1980 | Samain et al. ................ 568/908 |
| 2006/0193880 A1 | 8/2006 | Bedoukian .................... 424/405 |
| 2006/0193881 A1 | 8/2006 | Bedoukian .................... 424/405 |

OTHER PUBLICATIONS

Vanhaelen et al., Cellular and Molecular Life Sciences (Experientia), vol. 36, No. 4, pp. 406-407, Apr. 1980.

* cited by examiner

*Primary Examiner* — Mina Haghighatian
*Assistant Examiner* — Helen Chui
(74) *Attorney, Agent, or Firm* — Ohandt, Greeley, Ruggiero & Perle, LLP; George W. Rauchfuss, Jr.

(57) ABSTRACT

1,5-octadien-3-ol is an attractant for biting insects, particularly mosquitoes and may be used alone or with other attractants.

7 Claims, No Drawings

ATTRACTANT COMPOSITIONS AND METHOD FOR ATTRACTING BITING INSECTS

RELATED APPLICATION

This application claims priority of U.S. provisional Application No. 60/932,064 filed May 29, 2007.

FIELD OF THE INVENTION

The invention relates to improved compositions or systems for attracting mosquitoes and to methods for attracting biting insects, particularly mosquitoes and biting midges, employing such compositions and also to systems using such compositions for attracting mosquitoes and biting midges.

BACKGROUND TO THE INVENTION

Devices for attracting and destroying biting insects are well known in the art. While the prior art devices have employed a number of mechanisms and materials to attract insects, such as for example, heat, light, odor emitting substances, pheromones, kairomones and various chemicals, more recently it has been discovered that carbon dioxide alone or with other attractants such as octenol is particularly effective in attracting such insects. As examples of devices employing carbon dioxide and octenol are those devices disclosed in U.S. Pat. Nos. 5,205,064 and 6,055,766.

Researchers in the field of entomology have discovered that biting insects such as midges, biting flies and mosquitoes are attracted to blood hosts by the odor of kairomones, which are chemicals given off by the blood host and are attractants to such biting insects. Such kairomones include carbon dioxide exhaled by both avian and mammalian blood host and octenol, an alcohol which is given off by mammalian blood hosts. Mosquitoes and biting flies can detect the odor of carbon dioxide given off by a blood host at distance of approximately 90 meters. Biting insects locate a blood host by tracking the carbon dioxide plume created by a blood host. It has been discovered that a mixture of carbon dioxide and octenol is especially attractive to insects seeking mammalian blood hosts.

In the apparatus and devices heretofore proposed for attracting and/or destroying biting insects, the apparatus and devices rely upon a pressurized canister charged with carbon dioxide or propane/natural gas to generate carbon dioxide, or octenol and, preferably both carbon dioxide and octenol, with or without other semiochemicals or other attractants, to supply the attractant materials to the apparatus or device. However, there are various disadvantages associated with the use of such canisters. Among those disadvantages is the fact that the canister generally is very limited in size and need to be constantly replaced. With the need for replacement the apparatus and device cannot readily be placed in remote locations without the necessity for frequent trips to the location for canister monitoring and replacement. It would therefore be quite beneficial for a reduced amount of carbon dioxide that needs to be provided for effective attraction of biting insects, and to generally improve attraction of existing devices.

SUMMARY OF THE INVENTION

It has been discovered that the attractiveness of biting insects, particularly mosquitoes, to carbon dioxide-containing systems and traps can be improved if 1,5-octadien-3-ol is employed with carbon dioxide.

The invention is further characterized by a method for attracting biting insects comprising emitting from a trap or system an attractive effective amount of carbon dioxide and a further attractant component which is a 1,5-octadien-3-ol compound.

DETAILED DESCRIPTION OF THE INVENTION AND PREFERRED EMBODIMENTS

In accordance with this invention the attractiveness of biting insects, particularly mosquitoes, to carbon dioxide-containing systems or traps can be improved and increased if a 1,5-octadien-3-ol compound is employed along with carbon dioxide in the systems or traps.

The invention is further characterized by a method for attracting biting insects, particularly mosquitoes, comprising emitting from a trap or system an attractive effective amount of carbon dioxide and a further attractant comprising a 1,5-octadien-3-ol compound.

The components to be added to the carbon dioxide-containing systems or traps can be added in any suitable manner. Any suitable effective amount of the 1,5-octadien-3-ol component may be employed with the carbon dioxide, the amount being readily determined for any specific form of the 1,5-octadien-3-ol component and any insect to be attracted.

The 1,5-octadien-3-ol component may be employed in any suitable structural form or mixture of structural forms. For example, the 1,5-octadien-3-ol component may be a racemic mixture, one of the racemates, and in either the cis or trans form. Thus, the 1-5-octadien-3-ol component may be, for example, any of 1,5-octadien-3-ol (unspecified), 1,5Z-octadien-3-ol, r-1,5-octadien-3-ol and r-1,5Z-octadien-3-ol, as well as any combination of these and other 1,5-octadien-3-ol compounds.

The 1,5-octadien-3-ol compounds to be employed in this invention can be obtained from any suitable source. For example, 1,5-octadien-3-ol may be produced in the following manner. Cis linolenic acid or a fraction rich in linolenic acid is isolated by extraction of beer raw material, such as hop, malt or cereal. This linolenic acid is then subjected to lipoxygenase and lyase catalysis according to the method described by M. Wurzenburger and W. Grosch, Lipids, 21, 261 (1982), and by R. Tresel, D. Bahri and K. H. Engel, J. Agric. Food Chem., 30, 89 (1982) to produce 1,5-octadien-3-ol. (R)-1,5Z-octadien-3-ol; was obtained from Centre Ingredient Technology, Inc., McAdoo, Pa. 1,5Z-octadien-3-ol; may be obtained in the following manner. A nitrogen-purged reaction vessel is charged with 2 L of 1.6 M vinylmagnesium chloride in tetrahydrofuran (THF). To this stirred solution is fed a solution of 320 grams Z-3-hexenal in 0.8 L tetrahydrofuran over about 1.3 hours maintaining the reaction temperature between 25° and 30° C. After the reaction is complete, the mixture is poured into 2 L of cold saturated ammonium chloride solution. After thorough mixing and phase separation the aqueous layer is drained and the organic layer washed with 2 L of saturated ammonium chloride solution. The solvent is distilled off the product then the product is vacuum distilled at 0.5 mmHg through a short Vigreux column to give 291 grams of 1,5Z-octadien-3-ol.

The 1,5-octadien-3-ol attractants of this invention may be employed in combination with any other suitable known attractants, such as for example, including but not limited to $CO_2$, 1-octen-3-ol or r-1-octen-3-ol, $NO_2$, ammonia, and the like.

The 1,5-octadien-3-ol attractant compounds of this invention may be employed in any suitable formulation suitable for dispensing attractant effective amounts of the 1,5-octadien- 3-ol compounds. The compounds will generally be employed in formulations comprising a suitable medium, carrier or vehicle containing the attractant compounds. For example, the 1,5-octadien-3-ol. attractant compounds can be formulated in a specially formulated waxy or wax-like medium or vehicle engineered to release desired amounts of vaporous attractant compound at ambient temperatures, such as those mediums or vehicles available from Koster Keunen of Watertown, Conn. Alternatively, the 1,5-octadien3-ol attractant compound can be formulated in a porous medium or vehicle suitable for releasing effective amounts of the attractant compound. As an example of such porous medium or vehicle is a polyester membrane material having micropores encasing a block of inhibiting compound saturated fibers that gradually releases the inhibiting compound so that it permeates the microporous membrane and is released to the environment. Also the 1,5-octadien-3-ol compounds may be diluted in a vehicle such as diethyl phthalate (DEP) and employed as such. Another example is to incorporate the 1,5-octadien-3-ol compounds in a plastic matrix.

The attractant compounds can be placed in or on any suitable trap or system adapted to attract and trap the biting insect and for dispensing the attractant component.

Any suitable insect trap or system may be employed, such as for example, those traps and systems disclosed in U.S. Pat. Nos. 5,205,064, 6,055,766, and 6,145,243, incorporated herein by reference thereto. Such systems or traps normally employ about 100 to about 500 ml/min of carbon dioxide when in operation.

Although, as stated above, this invention may be employed with any suitable trap or system, the invention has been tested and employed in a trap or system as described hereinafter. Mosquito traps Model 1012 manufactured by John W. Hock Company in Gainesville, Fla. were used in these tests. The traps use a stream of $CO_2$ directed in the vicinity of a collection bag, with a fan used to blow mosquitoes into the bag. The light supplied to the trap was turned off. The traps were spaced 65-70 feet apart at the edge of a wetland in Danbury, Conn., at least 25 feet from any buildings. The 1,5-octadien-3-ol component was incorporated into a wax lure of the type manufactured by BioSensory, Inc. and placed near a stream of $CO_2$ which was being released at a rate of approximately 150 ml/minute. The traps were operated from approximately 4:00 PM until 9:00 AM the next day. Daytime temperatures were approximately 70-75° F. during the trials.

The invention is illustrated by, but not limited to, the following examples demonstrating the effectiveness of the invention.

Example 1

To establish a baseline control the Hock traps with just $CO_2$, and no added 1,5-octadien-3-ol component, were operated in the two areas on three days. The trap in area 1 (Trap A) caught 32 of the mosquitoes caught, and the trap in area 2 (Trap B) caught 23 of the mosquitoes caught. These control evaluations establish that area 1 (Trap A) is the more active mosquito area and provides a baseline catch ratio of 1.4 times as many mosquitoes as area 2 (Trap B). Tests were then run where Traps A was modified to include 1,5Z-octadien-3-ol in the trap in addition to the 150 ml/minute flow of $CO_2$ whereas for Trap B no 1,5-octadien-3-ol component was employed, just the 150 ml $CO_2$. For a four day test period Trap A caught 84 mosquitoes and trap B 35 mosquitoes. Trap A with the 1,5Z-octadien-3-ol. component caught 2.4 more mosquitoes than Trap B, a significant improvement over the 1.4 baseline catch ratio of the traps.

Example 2

This test was conducted over a twelve-day period. The test was conducted to determine if 1,5-octadien-3-ol increases the trap catch of mosquitoes when added to a trap already containing the known attractant r-1-octen-3-ol. Traps A in area 1 and B in area 2, as described in Example 1, were employed. Both traps A and B were tested with (1) 0.2 g 100% r-1-octen-3-ol+0.04 g r-1,5Z-octadien-3-ol. in 2 ml diethyl phthalate, and (2) with 2 g 100% r-1-octen-3-ol in 2 ml diethyl phthalate (i.e., with no 1,5Z-octadien-3-ol present). Over the twelve day test period the traps with the 1,5z-octadien-3-ol present caught 239 mosquitoes and the traps without the 1,5Z-octadien-3-ol present caught 221 mosquitoes. Thus, the presence of the 1,5Z-octadien-3-ol increased the catch of mosquitoes by 8%.

The ability of 1,5-octadien-3-ol to attract mosquitoes has also been confirmed by the electrophysiology test conducted under the direction of Dr. Walter S. Leal on behalf of the present inventor and reported in the article "Maxillary Pulps are Broad Spectrum Odorants in Culex quinquefasciatus", Z. Syed and W. Leal, *Chem. Senses* 32: 727-738, 2007.

While the invention has been described herein with reference to the specific embodiments thereof, it will be appreciated that changes, modification and variations can be made without departing from the spirit and scope of the inventive concept disclosed herein. Accordingly, it is intended to embrace all such changes, modification and variations that fall with the spirit and scope of the appended claims.

We claim:

1. A method for attracting biting insects comprising emitting from a trap or system an amount of a 1,5-octadien-3-ol component.

2. A method according to claim 1 wherein the 1,5-octadien-3-ol component is 1,5Z-octadien-3-ol.

3. A method according to claim 1 wherein the 1,5-octadien-3-ol component is r-1,5-octadien-3-ol.

4. A method according to claim 1 wherein the 1,5-octadien-3-ol component is r-1,5Z-octadien-3-ol.

5. A method according to claim 1 additionally containing carbon dioxide as an attractant.

6. A method according to claim 1 additionally containing 1-octen-3-ol as an attractant.

7. A method according to claim 1 additionally containing carbon dioxide and 1-octen-3-ol as attractants.

* * * * *